United States Patent [19]

Taylor

[11] 4,328,205
[45] May 4, 1982

[54] INHIBITION OF CORROSION OF ALUMINIUM TUBES BY TOOTHPASTES

[75] Inventor: Charles J. Taylor, London, England

[73] Assignee: Beecham Group Limited, England

[21] Appl. No.: 230,688

[22] Filed: Feb. 2, 1981

Related U.S. Application Data

[63] Continuation of Ser. No. 46,786, Jun. 8, 1979, abandoned.

[30] Foreign Application Priority Data

Jul. 12, 1978 [GB] United Kingdom ............... 29588/78

[51] Int. Cl.$^3$ .......................... A61K 7/18; A61K 7/16
[52] U.S. Cl. ........................................ 424/52; 424/49; 206/524.4; 206/524.5
[58] Field of Search ................................... 424/49–58; 206/524.4, 524.5

[56] References Cited

U.S. PATENT DOCUMENTS

| | | | |
|---|---|---|---|
| 3,538,230 | 11/1970 | Pader et al. | 424/50 |
| 3,678,155 | 7/1972 | Clippendale et al. | 424/52 |
| 3,689,637 | 9/1972 | Pader | 424/52 |
| 3,864,470 | 2/1975 | Watson | 424/52 |
| 3,937,321 | 2/1976 | Delaney | 424/52 |
| 3,980,767 | 9/1976 | Chowns et al. | 424/52 |
| 4,034,076 | 7/1977 | Coulson et al. | 424/52 |
| 4,140,757 | 2/1979 | Wason | 424/49 |
| 4,141,969 | 2/1979 | Mitchell | 424/52 |
| 4,144,322 | 3/1979 | Cordon et al. | 424/52 |
| 4,159,280 | 6/1979 | Wason | 424/52 |
| 4,174,387 | 11/1979 | Cordon et al. | 424/52 |

*Primary Examiner*—Shep K. Rose
*Attorney, Agent, or Firm*—Jacobs & Jacobs

[57] ABSTRACT

The tendency of gel toothpastes comprising silica thickeners, such as silica aerogel or precipitated silica, and a fluoride source, such as sodium monofluorophosphate or fluoride, to corrode aluminium tubes can be reduced by incorporating at least 0.01% by weight sodium or potassium hydroxide or carbonate, so that the pH of the toothpaste is at least 8.5.

11 Claims, No Drawings

INHIBITION OF CORROSION OF ALUMINIUM TUBES BY TOOTHPASTES

CROSS-REFERENCE

This is a continuation of Ser. No. 046,786 filed June 8, 1979, now abandoned.

This invention relates to the inhibition of corrosion of aluminium tubes by gel toothpastes containing silica and fluoride.

Gel toothpastes comprising silica and a source of fluoride ions are often extremely corrosive to the aluminium tubes in which they are usually packed. This corrosion results, among other things, in the production of gas in the tubes and dye fading in the toothpaste.

One common method of preventing such corrosion is to coat the internal surfaces of the tubes with an inert film, for example lacquer or plastic laminate. However, lacquer and plastic laminate coatings add substantially to the cost of the tubes, and, particularly in the case of lacquer, slight imperfections in the protective coat are common, so that protection is not complete.

It is widely accepted that aluminium is more susceptible to corrosion at low or high pH, so that corrosion is less likely to occur at, for example, pH 6–8 than at higher or lower pH. (See, for example, British Pat. No. 1,491,211).

However, we have now discovered that gel toothpastes comprising a fluoride source and a silica thickener are less likely to cause corrosion of the aluminium tubes in which they are packed if sodium or potassium hydroxide or sodium or potassium carbonate is incorporated in the toothpaste, despite the fact that the final product has a high pH.

Accordingly, this invention provides a method of inhibiting corrosion of aluminium tubes by gel toothpastes comprising a fluoride source and a silica thickener, which method comprises the incorporation in the toothpaste of at least 0.01% by weight, based on the weight of the toothpaste, of sodium or potassium hydroxide or sodium or potassium carbonate, so that the pH of the toothpaste is at least 8.5.

When sodium or potassium hydroxide is used, it will normally be at a level of up to 1%, more suitably 0.05 to 0.4% by weight of the toothpaste.

When sodium or potassium carbonate is used, it will normally be at a level of up to 1.5%, more suitably 0.1 to 1.0% by weight of the toothpaste.

When used herein, the term "fluoride source" means a source of free fluoride ions and/or monofluorophosphate ions. Examples of fluoride sources include sodium or ammonium monofluorophosphate, stannous fluoride and sodium or ammonium fluoride.

The toothpaste will normally contain at least 0.1% by weight of silica thickener. Suitable silicas for use as thickeners include grades of silica aerogels and precipitated silicas, having a small average particle size and little or no abrasive properties, as is well understood by those skilled in the art of toothpaste formulation.

The method of the invention is particularly useful when, in addition to the silica thickener, the toothpaste also comprises a synthetic clay thickener, such as synthetic smectite. Examples of synthetic smectites which have found use as thickeners in toothpastes are magnesium lithium silicates, such as those sold under the Trade Marks "Laponite" and "Barasym", and magnesium aluminium silicates, also sold under the Trade Mark "Barasym".

The following Example illustrates the invention.

EXAMPLE

Collapsible aluminium tubes were filled with certain translucent gel formulations, described below, and stored at room temperature or at 50° C. The tubes were then examined for swelling, gas production, dye fading and corrosion of the tube surface. The results are shown in Table 1.

Formulations 1A, 1B

|  | % by weight |
|---|---|
| 70% Sorbitol | 60 |
| Synthetic magnesium lithium silicate | 3.9 |
| Sodium carboxymethylcellulose | 1.3 |
| Polyethylene glycol | 4.0 |
| Silica aerogel | 2.0 |
| Sodium lauryl sulphate | 1.7 |
| Sodium monofluorophosphate | 0.8 |
| Color, flavour, preservative | 1.5 |
| Sodium hydroxide | 0 (A) or 0.2 (B) |
| Water | to 100 |

Stored at room temperature for 2 years.

Formulations 2A, 2B were as above, except that they contained no synthetic clay and a total of 8% silica aerogel.

Stored at 50° C. for 23 days.

Formulations 3A, 3B were as formulations 1A and 1B, except that they contained 0 and 0.5% of potassium hydroxide, respectively, in place of the sodium hydroxide.

Stored at 50° C. for 31 days.

Formulations 4A, 4B were as formulations 1A and 1B, except that they contained 4% precipitated silica in place of the silica aerogel.

Stored at 50° C. for 27 days.

Formulations 5A, 5B were as formulations 1A and 1B, except that they contained 3.9% of synthetic magnesium aluminium silicate in place of the magnesium lithium silicate.

Stored at 50° C. for 25 days.

Formulations 6A, 6B were as formulations 1A and 1B, except that they contained 0 and 1.05% sodium carbonate respectively, in place of the sodium hydroxide.

Stored at 50° C. for 5 days.

Formulations 7A, 7B were as formulation 1B, except that they contained 0.02% and 0.05% of sodium hydroxide, respectively.

Stored at 50° C. for 6 days.

NOTE: In the above formulations, the customary dental polishing agent has been omitted to make standardisation of the test easier and to facilitate measurement of, for example, dye fading. Practical toothpastes based on these formulations would normally contain a finely divided polishing agent such as calcium carbonate (perhaps applied as stripes on a given gel formulation) or silica xerogel (dispersed throughout the formulations to produce a translucent product).

| Formulation | pH | Swelling* | Gas | Fading* | Corrosion |
|---|---|---|---|---|---|
| 1A | 8.2 | +3 to +5 | Severe | −4 | Slight tarnish |
| 1B | 9.4 | 0 | None | 0 | None |

-continued

| Formulation | pH | Swelling* | Gas | Fading* | Corrosion |
|---|---|---|---|---|---|
| 2A | 6.7 | 0 to +3 | Slight | −3½ | Severe tarnish |
| 2B | 9.1 | 0 | None | 0 | None |
| 3A | 8.1 | +3 to +5 | Severe | −3 | Slight tarnish |
| 3B | 9.9 | 0 | None | 0 | None |
| 4A | 8.1 | +3 to +5 | Severe | −3 | Slight tarnish |
| 4B | 9.1 | | None | 0 | None |
| 5A | 7.9 | +3 to +5 | Moderate to severe | −3 | Severe tarnish |
| 5B | 9.7 | 0 | None | 0 | None |
| 6A | 8.4 | +2 to +4 | Moderate | −2 | Slight tarnish |
| 6B | 9.8 | 0 | None | 0 | None |
| 7A | 8.6 | 0 to +1 | None | 0 | None |
| 7B | 8.9 | 0 | None | 0 | None |

*Swelling scores are 0 (no detectable swelling) to 5 (tube crimp about to open)
Fading scores are 0 (no fading) to −5 (completely colourless)

I claim:

1. A method of inhibiting corrosion of unlined aluminium tubes by clear or translucent gel toothpastes comprising a fluoride source and a silica thickener, which method comprises the incorporation in the toothpaste of at least 0.01% by weight, based on the weight of toothpaste, of sodium or potassium hydroxide or sodium or potassium carbonate, so that the pH of the toothpaste is at least 8.5.

2. A method as claimed in claim 1 wherein sodium or potassium hydroxide is incorporated at a level of up to 1% by weight of the toothpaste.

3. A method as claimed in claim 2 wherein sodium or potassium hydroxide is incorporated at a level of from 0.05 to 0.4% by weight of the toothpaste.

4. A method as claimed in claim 1 wherein sodium or potassium carbonate is incorporated at a level of up to 1.5% by weight of the toothpaste.

5. A method as claimed in claim 4 wherein sodium or potassium carbonate is incorporated at a level of from 0.1 to 1.0% by weight of the toothpaste.

6. A method as claimed in claim 1 wherein the toothpaste in which the hydroxide or carbonate is incorporated contains sodium or ammonium monofluorophosphate or sodium, ammonium or stannous fluoride as fluoride source.

7. A method as claimed in claim 1 wherein the toothpaste in which the hydroxide or carbonate is incorporated contains a silica aerogel or precipitated silica thickener.

8. A method as claimed in claim 1 wherein the toothpaste in which the hydroxide or carbonate is incorporated contains a calcium carbonate dental polishing agent applied as one or more stripes on the surface of the gel.

9. A method as claimed in claim 1 wherein the toothpaste in which the hydroxide or carbonate is incorporated contains a silica xerogen dental polishing agent dispersed throughout the gel.

10. In a clear or translucent gel toothpaste comprising a fluoride source and a silica thickener packed in a collapsible unlined aluminum tube susceptible to corrosion, the improvement of including in said toothpaste as inhibitor of corrosion of aluminum an amount of sodium or potassium hydroxide or sodium or potassium carbonate sufficient to raise the pH of said toothpaste to at least pH 8.5, said amount being at least 0.01% of the weight of said toothpaste.

11. A toothpaste according to claim 10, wherein the fluoride source is sodium or ammonium monofluorophosphate or sodium, ammonium or stannous fluoride.

* * * * *